United States Patent [19]

Rentzea et al.

[11] Patent Number: 5,199,968
[45] Date of Patent: Apr. 6, 1993

[54] PLANT GROWTH REGULATORS CONTAINING OXALIC ACID DERIVATIVES

[75] Inventors: Costin Rentzea, Heidelberg; Wilhelm Rademacher, Limburgerhof; Michael Keil, Freinsheim; Albrecht Harreus, Ludwigshafen, all of Fed. Rep. of Germany

[73] Assignee: BASF Aktiengesellschaft, Ludwigshafen, Fed. Rep. of Germany

[21] Appl. No.: 848,503

[22] Filed: Mar. 9, 1992

Related U.S. Application Data

[62] Division of Ser. No. 737,740, Jul. 30, 1991, Pat. No. 5,163,992.

[30] Foreign Application Priority Data

Jul. 30, 1990 [DE] Fed. Rep. of Germany ....... 4024118

[51] Int. Cl.$^5$ ............................................. A01N 43/44
[52] U.S. Cl. ..................................... 504/209; 548/953
[58] Field of Search ............................ 71/88; 548/953

[56] References Cited

U.S. PATENT DOCUMENTS 4,944,789  7/1990  Rentzea et al. .................... 71/88

FOREIGN PATENT DOCUMENTS 275002  7/1988  European Pat. Off. .

Primary Examiner—Joseph Paul Brust
Assistant Examiner—Jacqueline Haley
Attorney, Agent, or Firm—Herbert B. Keil

[57] ABSTRACT

Oxalic acid derivatives of the formula I

A—CO—COO—Y—X—D    I where A is an unsubstituted or substituted azetidine ring which is bonded via its nitrogen atom, Y is unsubstituted or substituted alkylene, X is oxygen or sulfur and D is unsubstituted or substituted alkyl or alkenyl or is monocyclic or polycyclic unsubstituted or substituted cycloalkyl, cycloalkylmethyl, cycloalkenyl or cycloalkenylmethyl or unsubstituted or substituted phenyl, phenylalkyl or phenylalkenyl, their preparation and growth regulators containing them.

13 Claims, No Drawings

PLANT GROWTH REGULATORS CONTAINING OXALIC ACID DERIVATIVES

This is a divisional of application Ser. No. 07/737,740, filed Jul. 30, 1991 now U.S. Pat. No. 5,163,992.

The present invention relates to oxalic acid derivatives of the general formula I

A—CO—COO—Y—X—D        I where A is an azetidine ring which is bonded via its nitrogen atom and may carry one or two $C_1$–$C_3$-alkyl groups, Y is $C_2$–$C_{10}$-alkylene which may carry from one to three $C_1$–$C_3$-alkyl groups, X is oxygen or sulfur and D is $C_1$–$C_{20}$-alkyl or $C_3$–$C_{10}$-alkenyl, where these groups may carry from one to five halogen atoms, or is monocyclic or polycyclic $C_3$–$C_{10}$-cycloalkyl, $C_3$–$C_{10}$-cycloalkylmethyl, $C_5$–$C_{10}$-cycloalkenyl or $C_5$–$C_{10}$-cycloalkenylmethyl, where these rings may carry from one to three $C_1$–$C_4$-alkyl groups or a phenyl ring, or is phenyl, phenyl-$C_1$–$C_6$-alkyl or phenyl-$C_3$–$C_6$-alkenyl, where the aromic radicals may carry from one to five halogen atoms and/or from one to three of the following groups: nitro, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio or $C_1$–$C_4$-haloalkylthio.

The present invention furthermore relates to a process for the preparation of these oxalic acid derivatives, agents which contain them and methods for their use as plant growth regulators.

Oxalic acid derivatives are disclosed in the literature as intermediates for synthesis.

It is an object of the present invention to provide novel effective plant growth regulators.

We have found that this object is achieved by the oxalic acid derivatives I defined at the outset. We have furthermore found processes for the preparation of these oxalic acid derivatives, agents containing them and methods for their use as plant growth regulators.

The oxalic acid derivatives I are obtainable by various methods. They are particularly advantageously obtained by one of the processes A to D described below.

Process A:

Compounds of the formula I are obtained, for example, by reacting an oxalyl ester halide of the general formula II in a conventional manner (Caro et al., Chem. Ber. 63(1930), 1534) with an azetidine derivative of the general formula III in an inert organic solvent in the presence of a base.

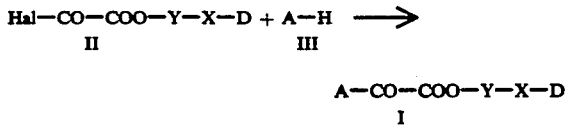

Hal—CO—COO—Y—X—D + A—H  ⟶
     II                III

A—CO—COO—Y—X—D
         I

In formula II, Hal is halogen, such as fluorine, chlorine, bromine or iodine, preferably chlorine or bromine.

The reaction is generally carried out at from −10° to 80° C., preferably from 0° to 50° C.

Examples of suitable solvents are halohydrocarbons, in particular chlorohydrocarbons, e.g. 1,1,2,2-tetrachloroethylene or 1,1,2,2-tetrachoroethane, dichloropropane, methylene chloride, dichlorobutane, chloroform, chloronaphthalene, dichloronaphthalene, carbon tetrachloride, 1,1,1- or 1,1,2-trichlorethane, trichloroethylene, pentachloroethane, o-, m- and p-difluorobenzene, 1,2-dichloroethane, 1,1-dichloroethane, 1,2-cis-dichloroethylene, chlorobenzene, fluorobenzene, bromobenzene, iodobenzene, o-, m- and p-dichlorobenzene, o-, m- and p-dibromobenzene, o-, m- and p-chlorotoluene and 1,2,4-trichlorobenzene, ethers, e.g. ethyl propyl ether, methyl tert-butyl ether, n-butyl ethyl ether, din-butyl ether, diisobutyl ether, diisoamyl ether, diisopropyl ether anisole, phenetole, cyclohexyl methyl ether, diethyl ether, ethylene glycol dimethyl ether, tetrahydrofuran, dioxane or thioanisole, nitrohydrocarbons, such as nitromethane, nitroethane, nitrobenzene, o-, m- and p-chloronitrobenzene, o-nitrotoluene; nitriles, such as acetonitrile, butyronitrile, isobutyronitrile, benzonitrile or m-chlorobenzonitrile, aliphatic or cycloaliphatic hydrocarbons, e.g. heptane, pinane, nonane or o-, m- or p-cumene, gasoline fractions boiling within a range of from 70° to 190° C., cyclohexane, methylcyclohexane, decalin, petroleum ether, hexane, naphtha, 2,2,4-trimethylpentane, 2,2,3-trimethylpentane, 2,3,3-trimethylpentane or octane, esters, e.g. ethyl acetate, ethyl acetoacetate or isobutyl acetate, amides, e.g. formamide, methylformamide or dimethyl formamide, ketones, e.g. acetone or methyl ethyl ketone, and if necessary also water and corresponding mixtures. The solvent is advantageously used in an amount of form 100 to 2,000, preferably from 200 to 700, % by weight, based on the starting material III.

Examples of suitable bases are potassium hydroxide, sodium hydroxide, potassium carbonate, sodium carbonate, lithium hydroxide, lithium carbonate, sodium bicarbonate, potassium bicarbonate, calcium hydroxide, calcium oxide, barium oxide, magnesium hydroxide, magnesium oxide, barium hydroxide, calcium carbonate, magnesium carbonate, magnesium bicarbonate, magnesium acetate, zinc hydroxide, zinc oxide, zinc carbonate, zinc bicarbonate, zinc acetate, sodium formate, sodium acetate, trimethylamine, trimethylamine, tripropylamine, triisopropylamine, tributylamine, triisobutylamine, trisec-butylamine, tri-tert-butylamine, tribenzylamine, tricyclohexylamine, triamylamine, trihexylamine, N,N-diemethylaniline, N,N-diethylaniline, N,N-dipropylaniline, N,N-dimethyltoluidine, N,N-diethyltoluidine, N,N-dipropyltoluidine, N,N-dimethyl-4-aminopyridine, N,N-dimethyl-4-aminopyridine, N,N-dipropyl-4-aminopyridine, N-methylpyrrolidine, N-ethylpyrrolidine, N-methylpiperidine, N-ethylpiperidine, N-methylpyrrolidone, N-methylimidazole, N-ethylimidazole, N-methylmorpholine, N-ethylmorpholine, N-methylhexamethyleneimine, N-ethylhexamethyleneimine, pyridine, quinoline, alpha-picoline, β-picoline, gamma-picoline, isoquinoline, pyrimidine, acridine, N,N,N',N'-tetramethylethylenediamine, N,N,N',N'-tetraethylethylenediamine, quinoxaline, quinazoline, N-propyldiisopropylamine, N,N-dimethylcyclohexylamine, 2,6-lutidine, 2,4-lutidine and triethylenediamine. Advantageously, the acid acceptor is used in a stoichiometric amount or in an amount which is grater than or less than the stoichiometric amount by not more than 20 mol %, based on the starting material II.

Process B:

The compounds of the formula I are also obtained, for example, by reacting an oxalyl amide halide of the general formula IV in a conventional manner with a compound of the general formula V in an inert organic solvent in the presence of a base.

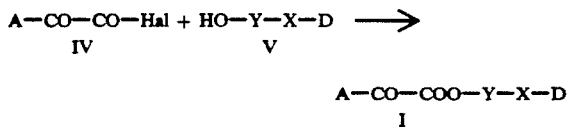

In formula IV, Hal is halogen, such as fluorine, chlorine, bromine or iodine, preferably chlorine or bromine.

The reaction is carried out in general at from −20° to 100° C., preferably from 0° to 80° C.

Suitable solvents and bases in this process are those stated above.

Process C:

The compounds of the formula I are furthermore obtained by reacting an oxalyl amide ester of the general formula VI in a conventional manner (Houben-Weyl, 4th Edition, Vol. 8, page 526 et seq.) with a compound of the general formula V in an inert organic solvent.

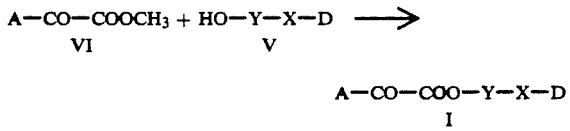

The reaction is carried out in general at from −10° to 150° C., preferably from 20° to 100° C.

Examples of suitable solvents are those stated above for process A. The stated alcohols are particularly suitable.

Suitable bases in this process in addition to those stated above are, in particular, sodium hydride and sodium methylate.

Process D:

In a further process, the compounds of the formula I are also obtained by reacting a salt of an oxalylamide of the general formula VII in a conventional manner (Houben-Weyl, 4th Edition, Vol. 8, page 542 et seq.) with a compound of the general formula VIII in an inert organic solvent.

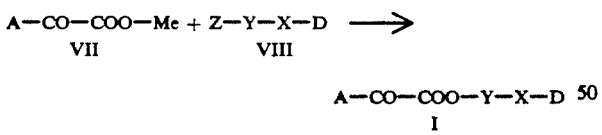

In formula VII, Me is an ion of an alkali metal such as lithium, sodium, potassium or cesium.

In formula VIII, Z is a nucleophilically displaceable leaving group such as halogen, e.g. chlorine, bromine or iodine, or alkyl- or arylsulfonyl, in particularly p-tolysulfonyl.

The reaction is carried out in general at from −10° to 150° C., preferably from 20° to 120° C.

Examples of suitable solvents are those stated above for process A. The following are particularly suitable: N,N-dimethylformamide, N,N-dimethylacetamide and N-methylpyrrolidone.

In this process, suitable bases in general and in particular are those stated above.

The novel oxalic acid derivatives of the formula I may contain centers of chirality. They are generally obtained as racemates and may be obtained as diastereomer mixtures. In the case of some of the novel compounds, pure diastereomers can be isolated in pure form, for example by column chromatography or on the basis of solubility differences. Pure racemates and enantiomers can be obtained from such purified diastereomers by known methods. The present invention relates to all these compounds and mixtures. Regarding the use of the novel azetidines as growth regulators, both the pure diastereomers or enantiomers and the mixtures thereof obtained in the synthesis are suitable. The latter are preferably used.

In view of the intended use of the compounds I, suitable substituents are the following radicals:

A is an azetidine ring which is bonded via its nitrogen atom and may carry one or two $C_1$–$C_3$-alkyl groups, such as methyl, ethyl, propyl or 1-methylethyl;

Y is a $C_2$–$C_{10}$-alkylene, such as ethylene, propylene, butylene, pentylene, hexylene, heptylene, octlyene, nonylene, or decylene, which may carry from one to three $C_1$–$C_3$-alkyl groups as stated above for A;

X is oxygen or sulfur; and

D is $C_1$–$C_{20}$- alkyl, such as methyl, ethyl, straight-chain or branched propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, preferably branched or straight-chain $C_1$–$C_6$-alkyl, such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2-2-trimethylpropyl, 1-ethyl-1-methylpropyl or 1-ethyl-2-methylpropyl; in particular branched or straight-chain $C_1$–$C_4$-alkyl, such as methyl, ethyl, propyl, 1-methylethyl, butyl, 1-methylpropyl, 2-methylpropyl or 1,1-dimethylethyl; or $C_3$–$C_{10}$-alkenyl, in particular $C_3$–$C_6$-alkenyl, such as 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethhyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl or 1-ethyl-2-methyl-2-propenyl;

where these groups may carry form one to five halogen atoms, such as fluorine, chlorine, bromine or iodine, preferably fluorine or chlorine;

monocyclic or polycyclic $C_3$–$C_{10}$-cycloalkyl, such as cyclopropyl, cyclobutyl, cyclopentyl, cyclohexyl, cycloheptyl, cyclooctyl, methyl, norbornyl, adamantyl or tricyclodecanyl;

monocyclic or polycyclic $C_3$–$C_{10}$-cycloalkylmethyl, such as cyclopropylmethyl, cyclobutylmethyl, cyclopentylmethyl, cyclohexylmethyl, cyclohpetylmethyl or cyclooctylmethyl; monocyclic or polycyclic $C_5$–$C_{10}$-cycloalkenyl, such as cyclopent-1-enyl, cyclopent-2-enyl, cyclopent-3-enyl, cyclohex-1-enyl, cyclohex-2-enyl, cyclohex-3-enyl, cyclohept-1-enyl, cyclohept-2-enyl, cyclohept-3-enyl, cyclohept-4-enyl, cyclooct-1-enyl, cyclooct-2-enyl, cyclooct-3-enyl and cyclooct-4-enyl; or monocyclic or polycyclic $C_5$–$C_{10}$-cycloalkenylmethyl, such as cyclopent-1-enylmethyl, cyclopent-2-enylmethyl, cyclopent-3-enylmethyl, cyclohex-1-enylmethyl, cyclohex-2-enylmethyl, cyclohex-3-enylmethyl, cyclohept-1-enylmethyl, cyclohept-2-enylmethyl, cyclohept-3-enylmethyl, cyclohept-4-enylmethyl, cyclooct-1-enylmethyl, cyclooct-2-enylmethyl, cyclooct-3-enylmethyl and cyclooct-4-enylmethyl;

where these saturated and monounsaturated rings may carry from one to three $C_1$–$C_4$-alkyl groups, such as methyl, ethyl, propyl, 1-methylethyl, butyl, 1-methylpropyl, 2-methylpropyl or 1,1-dimethylethyl, preferably methyl, 2-methylpropyl or dimethylethyl, in particular methyl, or a phenyl ring;

phenyl; phenyl-substituted $C_1$–$C_6$-alkyl as stated above, preferably $C_1$–$C_4$-alkyl, such as methyl, ethyl, propyl, 1-methylethyl, butyl, 1-methylpropyl, 2-methylpropyl or 1,1-dimethylethyl, preferably methyl, in particular methyl;

or phenyl-substituted $C_3$–$C_6$-alkenyl, such as 2-propenyl, 2-butenyl, 3-butenyl, 1-methyl-2-propenyl, 2-methyl-2-propenyl, 2-pentenyl, 3-pentenyl, 4-pentenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-2-propenyl, 1-ethyl-2-propenyl, 2-hexenyl, 3-hexenyl, 4-hexenyl, 5-hexenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-2-butenyl, 1,2-dimethyl-3-butenyl, 1,3-dimethyl-2-butenyl, 1,3-dimethyl-3-butenyl, 2,2-dimethyl-3-butenyl, 2,3-dimethyl-2-butenyl, 2,3-dimethyl-3-butenyl, 3,3-dimethyl-2-butenyl, 1-ethyl-2-butenyl, 1-ethyl-3-butenyl, 2-ethyl-2-butenyl, 2-ethyl-3-butenyl, 1,1,2-trimethyl-2-propenyl, 1-ethyl-1-methyl-2-propenyl 1-ethyl-2-methyl-2-propenyl;

where the aromatic radicals may carry from one to five halogen atoms, such as fluorine, chlorine, bromine or iodine, preferably fluorine or chlorine, and/or from one to three of the following groups: nitro, $C_1$–$C_4$-alkyl, such as methyl, ethyl, propyl, 1-methylethyl, butyl, 1-methylpropyl, 2-methylpropyl or 1,1-dimethylethyl; $C_1$–$C_4$-haloalkyl, in particular trifluoromethyl;

$C_1$–$C_4$-alkoxy, such as methoxy, ethoxy, propoxy, 1-methylethoxy, butoxy, 1-methylpropoxy, 2-methylpropoxy, or 1,1-dimethylethoxy; $C_1$–$C_4$-haloalkoxy, in particular difluoromethoxy or trifluoromethoxy; or $C_1$–$C_4$-alkylthio, such as methylthio, ethylthio, propylthio, 1-methylethylthio, butylthio, 1-methylpropylthio, 2-methylpropylthio or 1,1-dimethylethylthio.

Examples of particularly preferred oxalic acid derivatives of the general formula I are shown in the Table below.

TABLE

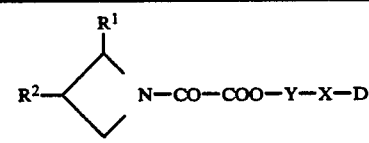

| D | Y | R¹ | R² | X |
|---|---|---|---|---|
| $CH_3$ | $CH_2$—$CH(CH_3)$ | H | H | O |
| $C_2H_5$ | $(CH_2)_2$ | H | H | O |
| $C_2H_5$ | $(CH_2)_2$ | $CH_3$ | H | O |
| $C_2H_5$ | $(CH_2)_2$ | H | H | S |
| $CH_3$ | $CH_2CH_2CH(CH_3)$ | H | H | O |
| n-$C_3H_7$ | $(CH_2)_2$ | H | H | O |
| i-$C_3H_7$ | $(CH_2)_2$ | H | H | O |
| $C_2H_5$ | $(CH_2)_3$ | H | H | O |
| n-$C_4H_9$ | $(CH_2)_2$ | $CH_3$ | $CH_3$ | O |
| n-$C_4H_9$ | $(CH_2)_3$ | H | H | O |
| n-$C_4H_9$ | $(CH_2)_2$ | H | H | S |
| n-$C_4H_9$ | $(CH_2)_4$ | H | H | O |
| n-$C_4H_9$ | $(CH_2)_6$ | H | H | O |
| n-$C_4H_9$ | $(CH_2)_8$ | H | H | O |
| sek.-$C_4H_9$ | $(CH_2)_4$ | H | H | O |
| sek.-$C_4H_9$ | $(CH_2)_4$ | $CH_3$ | H | O |
| sek.-$C_4H_9$ | $(CH_2)_{10}$ | H | H | O |
| i-$C_4H_9$ | $(CH_2)_4$ | H | H | O |
| i-$C_4H_9$ | $(CH_2)_5$ | H | H | O |
| n-$C_5H_{11}$ | $(CH_2)_2$ | H | H | O |
| n-$C_5H_{11}$ | $(CH_2)_3$ | H | H | O |
| n-$C_5H_{11}$ | $(CH_2)_8$ | H | H | O |

TABLE-continued $$\begin{array}{c} R^1 \\ | \\ R^2 \diamond N-CO-COO-Y-X-D \end{array}$$

| D | Y | $R^1$ | $R^2$ | X |
|---|---|---|---|---|
| $(CH_3)_3CCH_2$ | $(CH_2)_4$ | H | H | O |
| $(CH_3)_2CHCH_2CH_2$ | $(CH_2)_4$ | H | H | O |
| n-$C_6H_{13}$ | $(CH_2)_4$ | H | H | O |
| n-$C_6H_{13}$ | $(CH_2)_6$ | H | H | O |
| $(CH_3)_3CCH_2CH_2$ | $(CH_2)_4$ | H | H | O |
| n-$C_8H_{17}$ | $(CH_2)_4$ | H | H | O |
| 2-Ethylhexyl-1 | $(CH_2)_4$ | H | H | O |
| 2-Ethylhexyl-1 | $(CH_2)_6$ | H | H | O |
| 2-Ethylhexyl-1 | $(CH_2)_4$ | H | H | S |
| n-$C_{10}H_{21}$ | $(CH_4)_4$ | H | H | O |
| n-$C_{10}H_{21}$ | $(CH_2)_8$ | H | H | O |
| n-$C_{12}H_{25}$ | $(CH_2)_2$ | H | H | O |
| n-$C_{12}H_{25}$ | $(CH_2)_4$ | H | H | O |
| n-$C_{14}H_{29}$ | $(CH_2)_4$ | H | H | O |
| n-$C_{16}H_{33}$ | $(CH_2)_4$ | H | H | O |
| $CH_2=CHCH_2$ | $(CH_2)_2$ | H | H | O |
| $CH_2=CHCH_2$ | $(CH_2)_4$ | H | H | O |
| $CH_2=CHCH_2$ | $(CH_2)_4$ | $CH_3$ | H | O |
| $CH_2=CHCH_2$ | $(CH_2)_4$ | H | H | S |
| $ClCH=CHCH_2$ | $(CH_2)_4$ | H | H | O |
| $CH_2=CClCH_2$ | $(CH_2)_4$ | H | H | O |
| $CH_2=CBrCH_2$ | $(CH_2)_4$ | H | H | O |
| $CH_3CH=CHCH_2$ | $(CH_2)_4$ | H | H | O |
| Cl-$(CH_2)_3$ | $(CH_2)_4$ | H | H | O |
| Cl-$(CH_2)_4$ | $(CH_2)_4$ | H | H | O |
| Cl-$(CH_2)_6$ | $(CH_2)_4$ | H | H | O |
| Cl-$(CH_2)_8$ | $(CH_2)_4$ | H | H | O |
| Cyclopropyl | $(CH_2)_4$ | H | H | O |
| Cyclopropylmethyl | $(CH_2)_4$ | H | H | O |
| Cyclopropylmethyl | $(CH_2)_4$ | H | H | S |
| Cyclopentyl | $(CH_2)_4$ | H | H | O |
| Cyclopentyl | $(CH_2)_4$ | H | H | S |
| Cyclopentylmethyl | $(CH_2)_4$ | H | H | O |
| Cyclohexyl | $(CH_2)_2$ | H | H | O |
| Cyclohexyl | $(CH_2)_3$ | H | H | O |
| Cyclohexyl | $(CH_2)_4$ | H | H | O |
| Cyclohexyl | $(CH_2)_6$ | H | H | O |
| Cyclohexyl | $(CH_2)_8$ | H | H | O |
| Cyclohexyl | $(CH_2)_{10}$ | H | H | O |
| Cyclohexylmethyl | $(CH_2)_4$ | H | H | O |
| Cycloheptyl | $(CH_2)_4$ | H | H | O |
| 4-Methylcyclohexyl | $(CH_2)_4$ | H | H | O |
| 2-Methylcyclohexyl | $(CH_2)_4$ | H | H | O |
| 4-Isopropylcyclohexyl | $(CH_2)_4$ | H | H | O |
| 4-tert.-Butylcyclohexyl | $(CH_2)_4$ | H | H | O |
| 4-tert.-Butylcyclohexyl | $(CH_2)_6$ | H | H | O |
| 1-Decalyl | $(CH_2)_4$ | H | H | O |
| 2-Decalyl | $(CH_2)_4$ | H | H | O |
| 2-Norbornyl | $(CH_2)_4$ | H | H | O |
| 1,5-Dimethylbicyclo[2.3.1]octan-8-yl | $(CH_2)_4$ | H | H | O |
| Camphenyl | $(CH_2)_4$ | H | H | O |
| $C_6H_5-CH_2$ | $(CH_2)_2$ | H | H | O |
| $C_6H_5-CH_2$ | $(CH_2)_3$ | H | H | O |
| $C_6H_5-CH_2$ | $(CH_3)_4$ | H | H | O |
| $C_6H_5-CH_2$ | $(CH_2)_6$ | H | H | O |
| 4-F-$C_6H_4-CH_2$ | $(CH_2)_4$ | H | H | O |
| 4-Cl-$C_6H_4-CH_2$ | $(CH_2)_4$ | H | H | O |
| 4-Br-$C_6H_4-CH_2$ | $(CH_2)_4$ | H | H | O |
| 2,4-$Cl_2C_6H_4-CH_2$ | $(CH_2)_4$ | H | H | O |
| 3,4-$Cl_2C_6H_4-CH_2$ | $(CH_2)_4$ | H | H | O |
| 4-$CH_3C_6H_4-CH_2$ | $(CH_2)_4$ | H | H | O |
| 4-tert.-$C_4H_9C_6H_4-CH_2$ | $(CH_2)_4$ | H | H | O |
| 4-$F_3CC_6H_4-CH_2$ | $(CH_2)_4$ | H | H | O |
| 4-$O_2N-C_6H_4-CH_2$ | $(CH_2)_4$ | H | H | O |
| $C_6H_5-CH_2-CH_2$ | $(CH_2)_4$ | H | H | O |
| $C_6H_5-CH_2CH_2$ | $(CH_2)_6$ | H | H | O |
| $C_6H_5-CH_2CH_2CH_2$ | $(CH_2)_4$ | H | H | O |
| $C_6H_5-CH=CHCH_2$ | $(CH_2)_4$ | H | H | O |
| $C_6H_5-(CH_2)_4$ | $(CH_2)_4$ | H | H | O |
| $C_6H_5-CH_2CH(CH_3)CH_2$ | $(CH_2)_4$ | H | H | O |
| 4-tert.-$C_4H_9-C_6H_4-CH_2CH(CH_3)CH_2$ | $(CH_2)_4$ | H | H | O |

The novel growth-regulating compounds I or the agents containing them can be used, for example, in the form of directly sprayable solutions, powders, suspensions, including concentrated aqueous, oily or other suspensions or dispersions, emulsions, oil dispersions, pastes, dusting agents, broadcasting agents or granules, by spraying, atomizing, dusting, broadcasting or pouring. The application forms depend on the intended uses; they should in any case ensure very fine distribution of the novel active ingredients.

The compounds I are suitable in general for the preparation of directly sprayable solutions, emulsions, pastes or oil dispersions. Suitable inert additives are mineral oil fractions having a medium to high boiling point, such as kerosene or diesel oil, and coal tar oils and oils of vegetable or animal origin, aliphatic, cyclic and aromatic hydrocarbon, e.g., toluene, xylene, paraffin, tetrahydronaphthalene, alkylated naphthalenes or derivatives thereof, methanol, ethanol, propanol, butanol, cyclohexanol, cyclohexanone, chlorobenzene, isophorone or strongly polar solvents, such as N,N-dimethylformamide, dimethyl sulfoxide, N-methylpyrrolidone or water.

Aqueous application forms can be prepared from emulsion concentrates, dispersions, pastes, wettable powders or water-dispersible granules by adding water. For the preparation of emulsions, pastes or oil dispersions, the substrates, as such or dissolved in an oil or solvent, can be homogenized in water by means of wetting agents, adhesives, dispersants or emulsifiers. However, it is also possible to prepare concentrates which consist of active substance, wetting agents, adhesives, dispersants or emulsifiers and possibly a solvent or oil and which are suitable for dilution with water.

Suitable surfactants are alkali metal, alkaline earth metal and ammonium salts of aromatic sulfonic acids, e.g. lingin-, phenol-, naphthalene- and dibutylnaphthalenesulfonic acid, and of fatty acids, alkyl- and alkylarylsufonates, alkylsuflates, laurylethersulfates and fatty alcohol sulfates, and salts of sulfated hexa-, hepta- and octadecanols, and of fatty alcohol glycol ethers, condensates of sulfonated naphthalene and its derivatives with formaldehyde, condensates of naphthalene or of naphthalenesulfonic acids with phenol and formladehyde, polyoxyethylene octylphenol ethers, ethoxylated isooctyl-, octyl- or nonylphenol, alkylphenol polyglycol ethers, tributylphenol polyglycol ethers, alkylaryl polyether alcohols, isotridecyl alcohol, fatty alcohol/ethylene oxide condensates, ethoxylated castor oil, polyoxyethylene alkyl ethers or polyoxypropylene, lauryl alcohol polyglycol ether acetate, sorbitol esters, ligninsulfite waste liquors or methylcellulose.

Powders, broadcasting agents and dusting agents can be prepared by mixing or milling the active substances together with a solid carrier.

Granules, for example coated, impregnated and homogeneous granules, can be prepared by binding the active ingredients to solid carriers. Solid carriers are mineral earths, such as silica gel, silicas, silicates, talc, kaolin, limestone, lime, chalk, bole, loess, clay, dolomite, kieselguhr, calcium sulfate, magnesium sulfate or magnesium oxide, milled plastics, fertilizers, such as ammonium sulfate, ammonium phosphate, ammonium nitrate or ureas, and vegetable products, such as cereal meal, ground bark, woodmeal and nutshell meal, cellulose powder and other solid carriers.

The formulations contain from 0.1 to 95, preferably from 0.5 to 90, % by weight of active ingredient. The active ingredients are used in a purity of from 90 to 100%, preferably from 95 to 100% (according to the NMR spectrum).

The novel compounds I can be formulated, for example, as follows:

I. 90 parts by weight of compound No. 10 are mixed with 10 parts by eight of N-methyl-α-pyrrolidone, and a solution suitable for use in the form of very small drops is obtained.

II. 20 parts by weight of compound No. 13 are dissolved in a mixture which consists of 80 parts by weight of xylene, 10 parts by weight of the adduct of from 8 to 10 moles of ethylene oxide with 1 mole of oleic acid N-monoethanolamide, 5 parts by with of the calcium salt of dodecylbenzenesulfonic acid, 5 parts by weight of the adduct of 40 moles of ethylene oxide with 1 mole of castor oil. By pouring the solution into 100,000 parts by weight of water and finely distributing it therein, an aqueous dispersion which contains 0.02% by weight of the active ingredient is obtained.

III. 20 parts by weight of compound No. 10 are dissolved in a mixture which consists of 40 parts by weight of cyclohexanone, 30 parts by weight of isobutanol, 20 parts by weight of the adduct of 7 moles of ethylene oxide with 1 mole of isooctylphenol and 10 parts by weight of the adduct of 40 moles of ethylene oxide with 1 mole of castor oil. By pouring the solution into 100,000 parts by weight of water and finely distributing it therein, an aqueous dispersion which contains 0.02% by weight of the active ingredient is obtained.

IV. 20 parts by weight of active ingredient No. 13 are dissolved in a mixture which consists of 25 parts by weight of cyclohexanone, 65 parts by weight of a mineral oil fraction boiling within a range from 210° to 280° C. and 10 parts by weight of the adduct of 40 moles of ethylene oxide with 1 mole of castor oil. By pouring the solution into 100,000 parts by weight of water and finely distributing it therein, an aqueous dispersion which contains 0.02% by weight of the active ingredient is obtained.

V. 20 parts by weight of active ingredient No. 14 are thoroughly mixed with 3 parts by weight of the sodium salt of diisobutylnaphthalene-α-sulfonic acid, 17 parts by weight of the sodium salt of a lignisulfonic acid obtained from a sulfite waste liquor and 60 parts by weight of silica gel powder and the mixture is milled in a hammer mill. B finely distributing the mixture in 20,000 parts by weight of water, a spray liquor which contains 0.1% by weight of the active ingredient is obtained.

VI. 3 parts by weight of active ingredient No. 14 are mixed with 97 parts by weight of finely divided kaolin. A dusting agent which contains 3% by weight of the active ingredient is obtained in this manner.

VII. 30 parts by weight of active ingredient No. 17 are thoroughly mixed with a mixture of 92 parts by weight of silica gel powder and 8 parts by weight of liquid paraffin, which was sprayed onto the surface of the silica gel. A formulation of the active ingredient having good adhesion is obtained in this manner.

VIII. 20 parts by weight of active ingredient No. 18 are thoroughly mixed with 2 parts by weight of the calcium salt of dodecylbenzenesulfonic acid, 8 parts by weight of a fatty alcohol polyglycol ether, 2 parts by weight of sodium salt of a phenol/urea/formaldehyde condensate and 68 parts by weight of a paraffinic mineral oil. A stable oily dispersion is obtained.

IX. 95 by weight of compound No. 19 are mixed with 5 parts by weight of N-methyl-α-pyrrolidone and a solution which is suitable for use in the form of very small drops is obtained.

The growth-regulating agents or the active ingredients can be applied by the preemergence or postemergence method. If the active ingredients are less well tolerated by certain crops, it is possible to use application methods in which the herbicides are sprayed with the aid of the sprayers in such a way that as far as possible the herbicides do not come into contact with the leaves of the sensitive corps while the active ingredients reach the leaves of the undesirable plants growing underneath or the uncovered soil surface (post-directed, lay-by).

The application rates of active ingredient are from 0.01 to 5, preferably from 0.05 to 1.0, kg/ha of active substance, depending on the season, target plants and state of growth.

The compounds of the formula I can influence virtually all stages of development of a plant in different ways and are therefore used as growth regulators. The wide range of activity of the plant growth regulators depends in particular a) on the plant species and variety,
b) on the time of application, based on the stage of development of the plant, and on the season,
c) on the place and method of application (for example seed dressing, soil treatment, foliage application or trunk injection in the case of trees),
d) on climatic factors, for example temperature, amount of precipitation, and also the length of day and light intensity,
e) on the nature of the soil (including fertilizer application),
f) on the formulation or application form of the active ingredient and finally
g) on the concentrations of active substance used.

Some of the wide range of possible applications of the novel plant growth regulators of the formula I in cultivation, agriculture and in horticulture are mentioned below.

A. The compounds which can be used according to the invention may be employed for inhibiting the vegetative growth of the plants, which is manifested in particular in a reduction in the growth in length. The treated plants accordingly have stunted growth; in addition, a darker leaf coloration is observed.

A reduced intensity of growth of grasses along road edges, hedges and canal banks and on lawn areas, such as parks, sports grounds, orchards, lawns and airfields, proves advantageous in practice, enabling labor-intensive and expansive grass cutting to be reduced.

The increase in the strength of crops susceptible to loading, such as cereals, corn, sunflowers and soybean, is also of economic interest. The resulting shortening and strengthening of the stem reduce or eliminate the danger of lodging (bending) of plants under unfavorable weather conditions before harvesting.

The use of growth regulators for inhibiting the growth in length and for changing the time of ripening of cotton is also important. This permits completely mechanized harvesting of this important crop.

In the case of fruit trees and other trees, growth regulators help to save the costs of cutting. In addition, the alternance of fruit trees can be broken by growth regulators.

By using growth regulators, it is also possible to increase or inhibit the lateral branching of the plants. This is of interest if it is intended to inhibit the formation of side shoots in favor of leaf growth, for example in tobacco plants.

The frost resistance can also be considerably increased by means of growth regulators, for example in winter rape. On the one hand, the growth in length and the development of a leaf or plant mass which is too luxuriant (and hence particularly susceptible to frost) are inhibited. On the other hand, the young rape plants are held back in the vegetative state of development after sowing and before the onset of the winter frosts, despite favorable growth conditions. This also eliminates the danger of frost to such plants, which tend to exhibit a premature decline in the inhibition of blooming and to go over to the generative phase. In other crops too, for example winter cereals, it is advantageous if the stocks are well tillered in the fall by treatment with novel compounds but do not enter the winter with growth which is too luxuriant. This makes it possible to avoid high sensitivity to frost and, owing to the relatively small leaf or plant mass, attack by various diseases (for example fungal disease). The inhibition of vegetative growth also permits denser planting of the soil in the case of many crops, so that it is possible to achieve a greater yield based on the soil area.

B. The growth regulators enable greater yields to be obtained, both of plant parts and of plant ingredients. For example, it is possible to induce the growth of larger amounts of buds, blossoms, leaves, fruits, seeds, roots and tubers, to increase the content of sugar in sugar beets, sugar cane and citrus fruits, to increase the protein content in cereals or soybean or to stimulate greater latex flow in rubber trees.

The compounds of the formula I may result in increased yields by intervening in the plant metabolism or by promoting or inhibiting vegetative and/or generative growth.

C. Finally, a shortening or lengthening of the stages of growth as well as acceleration or retardation of ripening of the harvested plant parts before or after the harvest can be achieved by means of plant growth regulators.

For example, facilitating harvesting is also of economic interest, this being permitted by concentrated dropping or a decrease in the adhesion to the tree in the case of citrus fruits, olives or other species and varieties of pomes, drupes and hardhsell fruit. The same mechanism, i.e. promotion of the formation of abscission tissue between the fruit or leaf party and the shoot part of the plant, is also essential for readily controllable defoliation of crops such as cotton.

D. Growth regulators can furthermore be used to reduce the water consumption of plants. This is particularly important for agricultural areas which have to be artificially irrigated at high cost, for example in arid or semiarid regions. By the use of the novel substances, the intensity of irrigation can be reduced and hence more economical farming carried out. Under the influence of growth regulators, there is better utilization of the available water becomes, inter alia, the extent of opening of the stomata is reduced, a thicker epidermis and cuticula are formed, root penetration of the soil is improved and the microclimate in the crop is advantageously affected by more compact growth.

The growth regulators of the formula I which are to be used according to the invention can be fed to the crops both via the seed (as seed dressings) and via the soil, i.e. through the roots and, particularly preferably, via the foliage by spraying.

Because of the high toleration by plants, the application rate can be greatly varied.

To broaden the action spectrum and to achieve synergistic effects, the novel compounds I can be mixed, and applied together, with many other herbicidal or growth-regulating active ingredients. Examples of suitable components for the mixture are diazones, 4H-3,1-benzoxazine derivatives, benzothiadiazinones, 2,6-dinitroanilines, N-phenylcrabamates, thiocarbamates, halocarboxylic acids, triazines, amides, ureas, diphenyl ether, triazinones, uracils, benzofuran derivatives, cycloheane-1,3-dione derivatives, quinolinecarboxylic acid derivatives, aryloxy- and hetaryloxyphenoxyphenoxypropionic acids and their salts, esters and amides and others.

It may also be useful to apply compounds I alone or as a mixture in combination with other crop protection agents, for example with pesticides or agents for controlling phytopathogenic fungi or bacteria. The miscibility with mineral salt solutions which are used for eliminating nutrient and trace element deficiencies is also of interest. Nonphytotoxic oils and oil concentrates may also be added.

EXAMPLES OF SYNTHESES

The methods described in the following examples of syntheses were used to obtain further compounds I, with appropriate modification of the starting compounds. The compounds thus obtained are listed in the Tables below, together with physical data.

EXAMPLE 1

Azetidineoxamide butoxyethyl ester 80 ml of 2-butoxyethanol and 17.2 g (0.12 mol) of azetidineoxamide methyl ester were stirred with 0.2 g of sodium methylate for 3 hours at 90° C. while passing in nitrogen. The mixture was cooled to 20° C., after which 250 ml of ether were added, the mixture was washed with 50 ml of water, dried over $Na_2SO_4$ and evaporated down under reduced pressure, and the residue was then subjected to fractional distillation.

12.6 g (45.8% of theory) of azetidineoxamide butoxyethyl ester were obtained as a colorless oil of boiling point 112°-144° C./0.3 mbar and $n_D^{22} = 1.4679$.

EXAMPLE 2

Azetidineoxamide 4-propoxybutyl ester 18 g (0.12 mol) of 4-propoxybutyl chloride were added to 90 ml of dimethylformamide and 20 g (0.12 mol) of azetidineoxamide potassium salt and the mixture was stirred for 3 days at 60° C. After cooling, the mixture was filtered under suction, the filtrate was evaporated down under reduced pressure, the residue was dissolved in 200 ml of methylene chloride and the solution was washed with 50 ml of water, dried over $Na_2SO_4$ and evaporated down. The residue was freed from the final traces of solvent after 4 hours at 90° C. and 0.2 mbar.

17.8 g (61% of theory) of azetidineoxamide 4-propoxybutyl ester were obtained as a colorless oil of $n_D^{22} = 1.4572$.

TABLE 1

$$R^2 \diamond R^1 \quad N-CO-COO-Y-X-D$$

| Example No. | D | Y | $R^1$ | $R^2$ | X | bp. (°C./mbar) Refractive |
|---|---|---|---|---|---|---|
| 3 | $CH_3$ | $CH_2-CH(CH_3)$ | H | H | O | 125-130/0.3 |
| 4 | $C_2H_5$ | $(CH_2)_2$ | H | H | O | 129-133/0.4 |
| 5 | $CH_3$ | $CH_2CH_2CH(CH_3)$ | H | H | O | 137-139/0.4 |
| 6 | $n-C_3H_7$ | $(CH_2)_2$ | H | H | O | 141-143/0.5 |
| 7 | $i-C_3H_7$ | $(CH_2)_2$ | H | H | O | 146-150/0.5 |
| 8 | $C_2H_5$ | $(CH_2)_3$ | H | H | O | 137-139/0.2 |
| 9 | $n-C_4H_9$ | $(CH_2)_2$ | H | H | S | 180-184/0.3 |
| 10 | $n-C_4H_9$ | $(CH_2)_4$ | H | H | O | 156-159/0.3 |
| 11 | $n-C_4H_9$ | $(CH_2)_6$ | H | H | O | 163-166/0.3 |
| 12 | $n-C_4H_9$ | $(CH_2)_8$ | H | H | O | 190-193/0.3 |
| 13 | sec.-$C_4H_9$ | $(CH_2)_4$ | H | H | O | $n_D^{22} = 1.4670$ |
| 14 | $i-C_4H_9$ | $(CH_2)_4$ | H | H | O | 152-153/0.3 |
| 15 | $i-C_4H_9$ | $(CH_2)_5$ | H | H | O | 161-163/0.4 |
| 16 | $(CH_3)_3C-CH_2$ | $(CH_2)_4$ | H | H | O | 170-172/0.4 |
| 17 | $CH_2=CH-CH_2$ | $(CH_2)_2$ | H | H | O | 131-133/0.3 |
| 18 | $CH_2=CH-CH_2$ | $(CH_2)_4$ | H | H | O | 137-139/0.3 |
| 19 | Cyclopentyl | $(CH_2)_4$ | H | H | O | 178-180/0.4 |
| 20 | Cyclohexyl | $(CH_2)_2$ | H | H | O | 171-173/0.4 |
| 21 | Cyclohexyl | $(CH_2)_4$ | H | H | O | 179-183/0.3 |

USE EXAMPLES

The growth-regulating action of the compounds of the general formula I were demonstrated by the following experiments:

The acted ingredients were prepared
a) as a 0.1% strength solution in acetone or
b) as a 10% strength emulsion in a mixture of 70% by weight of cyclohexanol, 20% by weight of Nekanil ® LN (Lutensol ®AP6, wetting agent having an emulsifying and dispersing action and based on ethoxylated alkylphenols) and 10% by weight of Emulphor ®EL (Emulan ®EL, emulsifier based on ethoxylated fatty alcohols) and were diluted with acetone in the case of a) and with water in the case of b) to give the desired concentration.

The culture vessels used were plastic flowerpots (diameter about 12.5 cm; volume about 500 ml) containing loamy sand with about 3.0% of humus as a substrate. The seeds of the test plants were sown separately according to species.

In pre-emergence use, the active ingredients suspended or emulsified in water were applied directly after sowing by means of finely distributing nozzles. The vessels were lightly watered in order to promote germination and growth and then covered with transparent plastic covers until the plants had begun to grow. Covering ensures uniform germination of the test plants.

For the post-emergence treatment, the test plants were not treated with the suspended or emulsified active ingredients until a height of growth of from 3 to 15 cm had been reached, depending on the form of growth.

The plants were kept at 10°-25° C. or 20°-35° C. according to species. The test period extended over from 2 to 4 weeks. During this time, the plants were tended and their reaction the individual treatments was evaluated.

The growth-regulating action observed was confirmed by measurement of the height of growth at the end of the experiment. The measured values thus obtained were expressed as a ratio to the height of growth of untreated plants. N-(2-Chloroethyl)-N,N,N-trimethylammonium chloride (Example A) was used as a comparative substance for evaluating the growth-regulating action.

The plants used in the greenhouse experiments were spring wheat (cv. Ralle), summer barley (cv. Aramir), rice (cv. Bahia), sunflowers (cv. Spanners Allzweck) and soybean (cv. Maple arrow).

In post-emergence use of 1.5 mg/vessel, compounds 1, 2, 3, 7, 8, 9, 13, 14 and 19 had a better action than the known growth-regulator A in spring wheat (cv. Ralle) and in summer barley (cv. Aramir) and compounds 1, 3, 7, 8 and 9 had a better action than said growth regulator in rice (cv. Bahia).

In post-emergence use of 6 mg/vessel, compounds 2 and 8 had a better action than the known growth regulator A in sunflowers (cv. Spanners Allzweck).

In post-emergence use of 0.5 mg/vessel, compounds 1, 2, 8 and 9 had a better action than the known growth regulator A in soybean (cv. Maple arrow).

We claim:

1. A method for regulating plant growth, wherein the soil, the plants or their seeds is or are treated with a growth regulating amount of an azetidine derivative of the general formula I

A—CO—COO—Y—X—D        I where A is an azetidine ring which is bonded via its nitrogen atom and may be optionally substituted by one or two $C_1$–$C_3$-alkyl groups, Y is $C_2$–$C_{10}$-alkylene which may be optionally substituted by from one to three $C_1$–$C_3$-alkyl groups, X is oxygen or sulfur and D is $C_1$–$C_{20}$-alkyl or $C_3$–$C_{10}$-alkenyl, where these groups may be optionally substituted by from one to five halogen atoms, or is monocyclic or polycyclic $C_3$–$C_{10}$-cycloalkyl, $C_3$–$C_{10}$-cycloalkylmethyl, $C_5$–$C_{10}$-cycloalkenyl or $C_5$–$C_{10}$-cycloalkenylmethyl, where these rings may be optionally substituted by from one to three $C_1$–$C_4$-alkyl groups or a phenyl ring, or is phenyl, phenyl-$C_1$–$C_6$-alkyl or phenyl-$C_3$–$C_6$-alkenyl, where the aromatic radicals may be optionally substituted by from one to five halogen atoms and/or from one to three of the following groups: nitro, $C_1$–$C_4$-haloalkyl, $C_1$–$C_4$-alkoxy, $C_1$–$C_4$-haloalkoxy, $C_1$–$C_4$-alkylthio or $C_1$–$C_4$-haloalkylthio.

2. The method of claim 1, wherein the soil or the plants are treated at an application rate of active ingredient of from 0.01 to 5 kg/ha.

3. The method of claim 1, wherein the soil or the plants are treated at an application rate of active ingredient of from 0.05 to 1.0 kg/ha.

4. The method of claim 1, wherein A is an azetidine ring which is bonded via its nitrogen atom, Y is $(CH_2)_2$, X is oxygen and D is n-$C_4$-$H_9$.

5. The method of claim 1, wherein A is an azetidine ring which is bonded via its nitrogen atom, Y is $(CH_2)_4$, X is oxygen and D is n-$C_3$-$H_7$.

6. The method of claim 1, wherein A is an azetidine ring which is bonded via its nitrogen atom, Y is $CH_2$-$CH(CH_3)$, X is oxygen and D is $CH_3$.

7. The method of claim 1, wherein A is an azetidine ring which is bonded via its nitrogen atom, Y is $(CH_2)_2$, X is oxygen and D is $C_2H_5$.

8. The method of claim 1, wherein A is an azetidine ring which is bonded via its nitrogen atom, Y is $(CH_2)_2$, X is oxygen and D is i-$C_3H_7$.

9. The method of claim 1, wherein A is an azetidine ring which is bonded via its nitrogen atom, Y is $(CH_2)_3$, X is oxygen and D is $C_2H_5$.

10. The method of claim 1, wherein A is an azetidine ring which is bonded via its nitrogen atom, Y is $(CH_2)_2$, X is sulfur and D is n-$C_4H_9$.

11. The method of claim 1, wherein A is an azetidine ring which is bonded via its nitrogen atom, Y is $(CH_2)_4$, X is oxygen and D is sec.-$C_4H_9$.

12. The method of claim 1, wherein A is an azetidine ring which is bonded via its nitrogen atom, Y is $(CH_2)_4$, X is oxygen and D is i-$C_4H_9$.

13. The method of claim 1, wherein A is an azetidine ring which is bonded via its nitrogen atom, Y is $(CH_2)_4$, X is oxygen and D is cyclohexyl.

* * * * *